(12) United States Patent
Gliner et al.

(10) Patent No.: US 10,119,837 B2
(45) Date of Patent: Nov. 6, 2018

(54) MAGNETIC-FIELD GENERATING CIRCUIT FOR A TRACKING SYSTEM

(71) Applicant: Biosense Webster (Israel) Ltd., Yokneam (IL)

(72) Inventors: Vadim Gliner, Haifa (IL); Yaron Ephrath, Karkur (IL); Alon Boumendil, Givat Nili (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 15/202,705

(22) Filed: Jul. 6, 2016

(65) Prior Publication Data

US 2018/0010928 A1   Jan. 11, 2018

(51) Int. Cl.
| | |
|---|---|
| G01D 5/20 | (2006.01) |
| A61B 5/06 | (2006.01) |
| A61B 34/20 | (2016.01) |
| A61B 5/00 | (2006.01) |
| A61B 18/14 | (2006.01) |
| A61B 18/00 | (2006.01) |

(52) U.S. Cl.
CPC .............. *G01D 5/20* (2013.01); *A61B 5/062* (2013.01); *A61B 5/743* (2013.01); *A61B 34/20* (2016.02); *A61B 18/1492* (2013.01); *A61B 2018/0022* (2013.01); *A61B 2018/00375* (2013.01); *A61B 2018/00577* (2013.01); *A61B 2034/2051* (2016.02)

(58) Field of Classification Search
CPC ....... G01B 7/14; A61B 5/743; A61B 18/1492; A61B 2018/00375; A61B 2018/0022; G01D 5/20
USPC ..................................................... 324/207.15
See application file for complete search history.

(56) References Cited

U.S. PATENT DOCUMENTS

| | | |
|---|---|---|
| 4,710,708 A | 12/1987 | Rorden et al. |
| 5,425,367 A | 6/1995 | Shapiro et al. |
| (Continued) | | |

FOREIGN PATENT DOCUMENTS

| | | |
|---|---|---|
| WO | 87/04801 A1 | 8/1987 |
| WO | 2006/121740 A2 | 11/2006 |
| (Continued) | | |

OTHER PUBLICATIONS

U.S. Appl. No. 14/578,807, filed Dec. 22, 2014.
Extended European Patent Search Report for corresponding European Patent Application EP 17179725.1, dated Nov. 7, 2017.

*Primary Examiner* — Patrick Assouad
*Assistant Examiner* — Haidong Zhang
(74) *Attorney, Agent, or Firm* — Notaro, Michalos & Zaccaria P.C.

(57) ABSTRACT

Described embodiments include apparatus that includes a signal generator and an electric circuit. The signal generator is configured to supply a signal having both a first dominant frequency and a second dominant frequency. The electric circuit, which includes a reactive component, is configured to generate, upon the signal being supplied to the electric circuit, a magnetic field having both the first dominant frequency and the second dominant frequency, by virtue of the reactive component simultaneously resonating at both the first dominant frequency and the second dominant frequency. Other embodiments are also described.

7 Claims, 2 Drawing Sheets

(56) References Cited

U.S. PATENT DOCUMENTS

| | | | |
|---|---|---|---|
| 5,680,047 A | * | 10/1997 | Srinivasan ......... G01R 33/3635 |
| | | | 324/318 |
| 6,223,066 B1 | | 4/2001 | Govari |
| 6,335,617 B1 | | 1/2002 | Osadchy et al. |
| 2004/0193057 A1 | | 9/2004 | Barbato et al. |
| 2007/0265526 A1 | | 11/2007 | Govari et al. |
| 2009/0082665 A1 | | 3/2009 | Anderson |
| 2010/0198058 A1 | | 8/2010 | Benson et al. |

FOREIGN PATENT DOCUMENTS

| WO | 2012-135421 A1 | 10/2012 |
|---|---|---|
| WO | WO 2013/149683 A1 | 10/2013 |

* cited by examiner

MAGNETIC-FIELD GENERATING CIRCUIT FOR A TRACKING SYSTEM

FIELD OF THE INVENTION

Embodiments of the present invention relate generally to the field of medical devices, and particularly, to the facilitation of the performance of a medical procedure by tracking the position and orientation of a tool used for the procedure.

BACKGROUND

US Patent Application Publication 2007/0265526, whose disclosure is incorporated herein by reference, describes a magnetic position tracking system for performing a medical procedure on a patient who is positioned on an upper surface of a table. The system includes a location pad, which is positioned on the upper surface of the table beneath the patient. The location pad includes one or more field generators, which are operative to generate respective magnetic fields and are arranged so that a thickness dimension of the location pad is no greater than 3 centimeters. A position sensor is fixed to an invasive medical device for insertion into a body of the patient, and is arranged to sense the magnetic fields so as to measure a position of the medical device in the body.

U.S. Pat. No. 5,425,367, whose disclosure is incorporated herein by reference, describes a system for externally locating the depth and orientation of a catheter in tissue with an external probe which generates a virtual rotating magnetic field. The catheter includes an inductive coil for developing an induced signal in response to the virtual rotating magnetic field. An indicating device such as a light bar display or digital readout indicates the strength of the induced signal for locating, independently of the relative angular orientation of the probe and the catheter, the depth in the tissue of the catheter.

U.S. Pat. No. 6,223,066, whose disclosure is incorporated herein by reference, describes an elongate medical probe, having proximal and distal ends, whose position is tracked within the body of a subject. The probe includes a magnetic-field responsive optical element adjacent to the distal end, which modulates light passing therethrough responsive to an externally-applied magnetic field. The probe also includes a fiberoptic coupled to receive modulated light from the optical element and convey it to the proximal end of the probe for analysis of the modulation.

U.S. Pat. No. 6,335,617, whose disclosure is incorporated herein by reference, describes a method for calibrating a magnetic field generator, including fixing one or more magnetic field sensors to a probe in known positions and orientations and selecting one or more known locations in the vicinity of the magnetic field generator. The magnetic field generator is driven so as to generate a magnetic field. The probe is moved in a predetermined, known orientation to each of the one or more locations, and signals are received from the one or more sensors at each of the one or more locations. The signals are processed to measure the amplitude and direction of the magnetic field, at the respective positions of the one or more sensors and to determine calibration factors relating to the amplitude and direction of the magnetic field in the vicinity of the magnetic field generator.

PCT Publication WO/2013/149683, whose disclosure is incorporated herein by reference, describes systems, devices and methods for the ablation of a ablation of the wall of one or more pulmonary veins (PV) from the inside, preferably transmural ablation and preferably at the level of the antrum. One or more implant devices can be implanted in the vessels and can subsequently be heated by external energy-providing means.

SUMMARY OF THE INVENTION

There is provided, in accordance with some embodiments of the present invention, apparatus that includes a signal generator and an electric circuit. The signal generator is configured to supply a signal having both a first dominant frequency and a second dominant frequency. The electric circuit, which includes a reactive component, is configured to generate, upon the signal being supplied to the electric circuit, a magnetic field having both the first dominant frequency and the second dominant frequency, by virtue of the reactive component simultaneously resonating at both the first dominant frequency and the second dominant frequency.

In some embodiments, the electric circuit includes a first resonant circuit configured to resonate at the first dominant frequency, and a second resonant circuit configured to resonate at the second dominant frequency, and the reactive component is common to both the first resonant circuit and the second resonant circuit.

In some embodiments, the reactive component is a first inductor, and the electric circuit further includes:
a first capacitor, connected in series with the first inductor;
a second inductor, connected in parallel with the first inductor; and
a second capacitor, connected in parallel with the first inductor and in series with the second inductor.

In some embodiments,
the first capacitor and the first inductor are configured to resonate, collectively, at the first dominant frequency, and
the second capacitor, the first inductor, and the second inductor are configured to resonate, collectively, at the second dominant frequency.

In some embodiments, the first capacitor is configured to have an impedance having a magnitude of less than 20 Ohm at the second dominant frequency, and the second capacitor is configured to have an impedance having a magnitude of greater than 1000 Ohm at the first dominant frequency.

In some embodiments, the electric circuit includes:
a coil; and
a coil tap, including the first capacitor, that taps the coil, the first and second inductors being respective portions of the coil that are on opposite sides of the coil tap.

In some embodiments, a difference between the first dominant frequency and the second dominant frequency is at least 5 kHz.

In some embodiments, the first dominant frequency is less than 5 kHz, and the second dominant frequency is greater than 15 kHz.

In some embodiments, the apparatus further includes:
at least one first sensor, configured to generate a first signal in response to sensing the magnetic field at the first dominant frequency; and
at least one second sensor, configured to generate a second signal in response to sensing the magnetic field at the second dominant frequency.

In some embodiments, the apparatus further includes an intrabody tool including the first sensor.

There is further provided, in accordance with some embodiments of the present invention, a method for generating a magnetic field. The method includes, using a signal generator, supplying, to an electric circuit that includes a reactive component, a signal having both a first dominant frequency and a second dominant frequency. The method further includes, using the electric circuit, generating, upon the signal being supplied to the electric circuit, a magnetic field having both the first dominant frequency and the second dominant frequency, by virtue of the reactive component simultaneously resonating at both the first dominant frequency and the second dominant frequency.

In some embodiments, the method further includes:

using at least one first sensor, generating a first signal in response to sensing the magnetic field at the first dominant frequency;

using at least one second sensor, generating a second signal in response to sensing the magnetic field at the second dominant frequency; and in response to the first signal and the second signal, ascertaining respective locations of the first sensor and the second sensor.

In some embodiments, using the first sensor to generate the first signal includes using the first sensor to generate the first signal while the first sensor is inside a body of a subject.

In some embodiments, generating the magnetic field includes generating the magnetic field from beneath the subject.

The present invention will be more fully understood from the following detailed description of embodiments thereof, taken together with the drawings, in which:

DETAILED DESCRIPTION OF EMBODIMENTS

Overview

Figure 1:
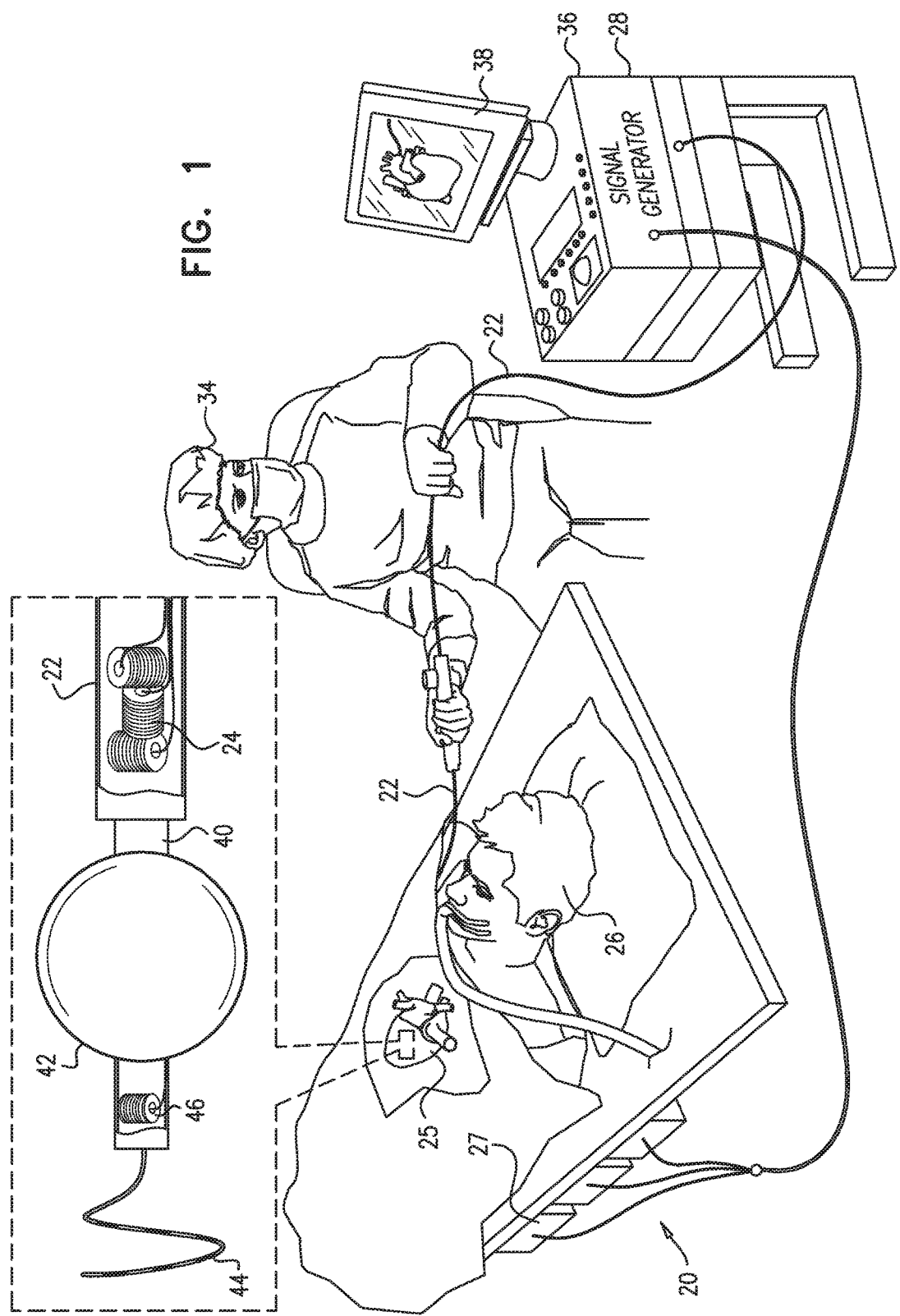
FIG. 1 is a schematic illustration of a magnetic tracking system, in accordance with some embodiments of the present invention.

As described in the aforementioned US Patent Application Publication 2007/0265526, whose disclosure is incorporated herein by reference, a magnetic position tracking system may be used for performing a medical procedure. Such a system comprises a plurality of magnetic-field generators, each of which is configured to generate a magnetic field at a respective frequency that is near a particular "base frequency." (For example, for a base frequency of 1 kHz, the generators may generate, respectively, at 1 kHz, 1.2 kHz, 1.4 kHz, etc.) Thus, during the procedure, the generators, which are positioned beneath the subject, collectively generate a magnetic field having a plurality of different dominant frequencies. An intrabody tool used for the procedure is provided with sensors, which sense the magnetic field, and generate signals (in the form of alternating voltages across the sensors induced by the magnetic field) in response thereto. In response to these signals, the respective positions and/or orientations of the sensors—and hence, the position and/or orientation of the intrabody tool—may be ascertained.

During some procedures, it may be desirable to simultaneously track the respective positions and/or orientations of differently-sized sensors. For example, a larger intrabody tool used for a particular procedure may be equipped with larger sensors, while a smaller intrabody tool used together with the larger intrabody tool may be equipped with smaller sensors. As a general rule, however, smaller sensors perform best with higher magnetic-field frequencies than those at which larger sensors perform best. It may thus be necessary to generate the magnetic field at twice the number of dominant frequencies: (i) for the smaller sensors, a first set of frequencies that are close to a larger base frequency (e.g., 17 kHz), and (ii) for the larger sensors, a second set of frequencies that are close to a smaller base frequency (e.g., 1 kHz). One hypothetical solution is to double the number of generators; however, this solution may not be practical, due to the increased amount of space occupied by, and/or power consumed by, the generators, and/or due to cost considerations.

Embodiments described herein therefore provide a superior solution, per which each magnetic-field generator may be used to simultaneously generate a magnetic field at two different dominant frequencies. Typically, each of the generators comprises an electric circuit, comprising a reactive component (i.e., an inductor or a capacitor) that is connected with other elements in the circuit such that, upon a suitable alternating signal being supplied to the electric circuit, the reactive component simultaneously resonates at both a first dominant frequency and a second dominant frequency. By virtue of the resonating of the reactive component, the electric circuit generates a magnetic field having both the first dominant frequency and the second dominant frequency.

For example, the electric circuit may comprise a first capacitor, a first inductor connected in series with the first capacitor, a second inductor connected in parallel with the first inductor, and a second capacitor connected in parallel with the first inductor and in series with the second inductor. In such embodiments, the first capacitor and the first inductor collectively resonate at the first frequency, while the second capacitor, the first inductor, and the second inductor collectively resonate at the second frequency.

Hence, using embodiments described herein, both the smaller sensors and larger sensors may be tracked, without needing to increase the number of generators.

System Description

Reference is initially made to FIG. 1, which is a schematic illustration of a magnetic tracking system 20, in accordance with some embodiments of the present invention.

FIG. 1 depicts a physician 34 performing a cardiac ablation procedure on a subject 26, using apparatus described, for example, in U.S. patent application Ser. No. 14/578,807, whose disclosure is incorporated herein by reference. First, a sheath 22 is inserted into the heart 25 of subject 26, and a catheter 40 is deployed from sheath 22 within the heart. Catheter 40 comprises, at its distal end, an expandable structure, such as a balloon 42, upon which a plurality of electrodes are disposed. Following the deployment of the catheter, a guide (or "lasso") 44 is used to stabilize the catheter by engaging the interior wall of a pulmonary vein, and the electrodes are then used to ablate the pulmonary vein. As described in detail below, during the procedure, system 20 tracks the position and/or orientation of both the distal end of sheath 22, and the distal end of catheter 40. Similarly, system 20 may be used to track the respective positions and/or orientations of any plurality of tools, e.g., intrabody tools, during any relevant procedure.

System 20 comprises a plurality of generating circuits 27 (also referred to herein as "generators") disposed underneath, or otherwise in the vicinity of, the subject. Generating circuits 27 are configured to collectively generate a magnetic field having a plurality of different dominant frequencies. During the procedure, a signal generator 28 in a console 36 supplies an alternating signal (typically, an alternating current), which includes the plurality of dominant frequencies, to each of the generating circuits. As further described below with reference to FIGS. 2A-B, the application of the alternating signal to the generating circuits causes the generating circuits to resonate at the dominant frequencies, thus generating the magnetic field.

The distal end of sheath 22 comprises a plurality of sensors 24, each one of sensors 24 comprising a coil. The generated magnetic field induces, across sensors 24, alternating voltages that include the plurality of dominant frequencies. Based on the respective amplitudes of these frequency components of the induced voltages, the position and/or orientation of the distal end of the sheath may be ascertained. Stated differently, sensors 24 generate signals in response to sensing the magnetic field, the signals indicating the position and/or orientation of the distal end of the sheath.

Similarly, the distal end of catheter 40 comprises a sensor 46, comprising a coil. The generated magnetic field induces an alternating voltage across sensor 46, such that, based on the respective amplitudes of the dominant frequency components of the induced voltage, the position and/or orientation of the distal end of the catheter may also be ascertained.

As depicted in FIG. 1, due to the smaller size of catheter 40 relative to sheath 22, sensor 46 is smaller than sensors 24. Therefore, as described above, sensor 46 requires a higher-frequency magnetic field than sensors 24. Hence, each generating circuit 27 simultaneously generates a magnetic field at two frequencies: a first, lower frequency for sensors 24, and a second, higher frequency for sensor 46.

For example, system 20 may comprise nine generating circuits, each of which is configured to simultaneously generate at both (i) a first frequency that is near a base frequency of 1 kHz, and (ii) a second frequency that is near a base frequency of 17 kHz. (FIG. 1 corresponds to such a nine-generator embodiment, assuming the nine generating circuits are arranged in three rows of three, with FIG. 1 showing the outermost row of three.) Thus, for example, the generators may be configured to collectively generate a magnetic field having (i) a first set of dominant frequencies of 1 kHz, 1.2 kHz, 1.4 kHz, 1.6 kHz, 1.8 kHz, 2 kHz, 2.2 kHz, 2.4 kHz, and 2.6 kHz, and (ii) a second set of dominant frequencies of 17 kHz, 17.2 kHz, 17.4 kHz, 17.6 kHz, 17.8 kHz, 18 kHz, 18.2 kHz, 18.4 kHz, and 18.6 kHz, by virtue of each generator simultaneously resonating at both one of the first set of frequencies and one of the second set of frequencies. Sensors 24 generate signals in response to sensing the magnetic field at the first set of frequencies, such that, by analyzing the components of the signals at the first set of frequencies, the respective positions and/or orientations of sensors 24—and hence, the position and/or orientation of sheath 22—may be ascertained. Likewise, sensor 46 generates a signal in response to sensing the magnetic field at the second set of frequencies, such that, by analyzing the components of the signal at the second set of frequencies, the position and/or orientation of sensor 46—and hence, of catheter 40—may be ascertained.

In general, each of the tracked intrabody tools may comprise any suitable number of sensors. Typically, although the tool position and orientation have, collectively, only six degrees of freedom, the total number of sensors and generators is greater than six, i.e., the system is "overdetermined." Thus, for example, sheath 22 comprises three sensors 24, despite the sheath, strictly speaking, requiring only one sensor. (Due to the smaller size of catheter 40, catheter 40 comprises only one sensor 46.)

In general, each of the generating circuits may be configured to resonate at any two relevant frequencies. The difference between the two frequencies may be relatively large (e.g., at least 5 kHz or 10 kHz, as in the example above), or smaller (e.g., less than 5 kHz).

Figure 2A:
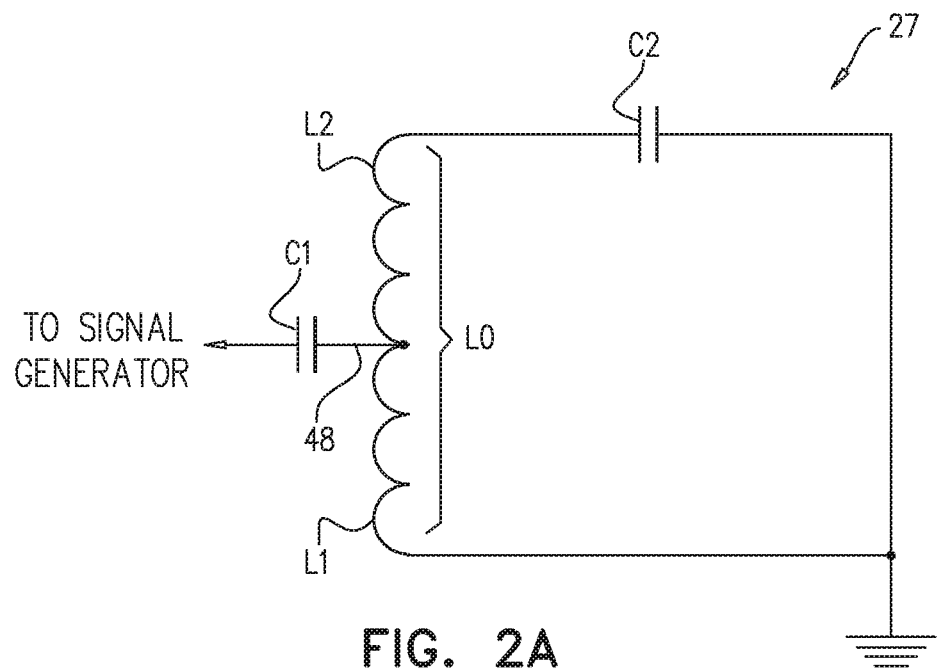
FIGS. 2A-B are schematic illustrations of generating circuits, in accordance with some embodiments of the present invention.
Figure 2B:
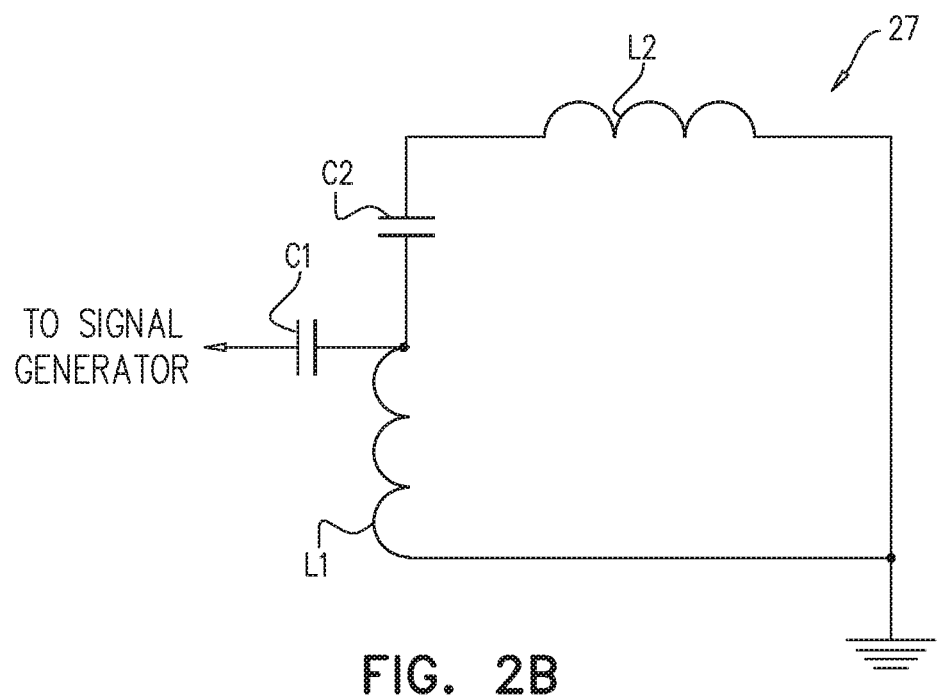

Reference is now made to FIGS. 2A-B, which are schematic illustrations of generating circuits 27, in accordance with some embodiments of the present invention. In general, the circuit shown in FIG. 2A is functionally equivalent to the circuit shown in FIG. 2B; the figures differ from one another only with respect to the layout of the circuit, as described below.

As described in detail below, generating circuit 27 is configured to resonate, in response to the supply to the circuit of an appropriate alternating signal from signal generator 28, at a lower resonant frequency, referred to below by the notation "f1," and also at a higher resonant frequency, referred to below by the notation "f2." In effect, as further described below, circuit 27 comprises two resonant circuits; the first resonant circuit resonates at f1, and the second resonant circuit resonates at f2.

In the particular examples shown in FIGS. 2A-B, generating circuit 27 comprises a first capacitor C1, a second capacitor C2, a first inductor L1, and a second inductor L2, which is coiled in the same orientation (i.e., clockwise or counterclockwise) as is first inductor L1. First inductor L1 and second inductor L2 are connected in parallel with one another, and in series with first capacitor C1, while second capacitor C2 is connected in parallel with first inductor L1 and in series with second inductor L2. In FIG. 2A, the circuit comprises a coil L0, which is tapped by a coil tap 48 comprising the first capacitor, such that the first and second inductors are respective portions of coil L0 that are on opposite sides of coil tap 48. In FIG. 2B, on the other hand, each of the first and second inductors comprises a respective separate coil, and the positions of the second capacitor and second inductor are interchanged, relative to FIG. 2A.

Each of the inductors belonging to circuit 27 may have any suitable shape; for example, each of the inductors may be barrel-shaped, or alternatively, flat. Also, each of the inductors may have any suitable dimensions; as a purely illustrative example, each inductor may be 5 cm×5 cm×3 cm.

The description below uses the notation "|C1|" to refer to the capacitance of first capacitor C1, "|C2|" to refer to the capacitance of second capacitor C2, "|L1|" to refer to the inductance of first inductor L1, and "|L2|" to refer to the inductance of second inductor L2.

In general, |C1|, |C2|, |L1|, and |L2| are selected such that:

(i) at frequencies near f2, the first capacitor effectively behaves as a short circuit (i.e., the magnitude of the impedance of the first capacitor is less than 20 Ohm), (ii) $1/(2\pi\sqrt{|L'|*|C2|})=f2$, where $L'=1/(1/|L1|+1/|L2|)$, (iii) at frequencies near f1, the second capacitor effectively behaves as an open circuit (i.e., the magnitude of the impedance of the second capacitor is greater than 1000 Ohm), and (iv) $1/(2\pi\sqrt{|L1|*|C1|})=f1$.

At frequencies near f1, circuit 27 functions as a "series LC resonance circuit," for which the resonant frequency is $1/(2\pi\sqrt{|L1|*|C1|})$. Therefore—given the appropriate selection of |L1| and |C1|—the first capacitor and first inductor collectively resonate at f1. Stated differently, the first capacitor and first inductor together form a first resonant circuit, which resonates at f1. On the other hand, at frequencies near f2, due to the first capacitor behaving as a short circuit, circuit 27 functions as a "parallel LC resonance circuit," for which the resonant frequency is $1/(2\pi\sqrt{|L'|*|C2|})$. Therefore—given the appropriate selection of |L1|, |L2|, and |C2|—the second capacitor, first inductor, and second inductor collectively resonate at f2. In other words, the second capacitor, first inductor, and second inductor together form a second resonant circuit, which resonates at f2. (The first inductor is common to both the first resonant circuit and the second resonant circuit.) Thus, as long as the signal supplied to the circuit includes both f1 and f2 frequency components, circuit 27 will simultaneously resonate at both f1 and f2.

For example, circuit 27 resonates at both 3.2 kHz and 16 kHz, if |C1|=750 nF, |C2|=60 nF, |L1|=3.3 mH, and |L2|=3.3 mH. In particular:

(i) At 16 kHz, the magnitude of the impedance of capacitor C1 is only 13.3 Ohm, i.e., C1 effectively functions as a short circuit.

(ii) $1/(2\pi\sqrt{|L'|*|C2|})$=16 kHz.

(iii) At 3.2 kHz, the magnitude of the impedance of capacitor C2 is 828.9 Ohm, i.e., C2 effectively functions as an open circuit.

(iv) $1/(2\pi\sqrt{|L1|*|C1|})$=3.2 kHz.

As described above, in the embodiments of FIGS. 2A-B, first inductor L1 simultaneously resonates at both the first dominant frequency and the second dominant frequency, i.e., L1 is common to both the first resonant circuit and the second resonant circuit. In other embodiments, the common reactive component is a capacitor, rather than an inductor. For example, the embodiments of FIGS. 2A-B may be modified by swapping the positions of C1 and L1, such that C1, rather than L1, simultaneously resonates at both the first dominant frequency and the second dominant frequency.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
a signal generator, configured to supply a signal having both a first dominant frequency and a second dominant frequency; and
an electric circuit, comprising a reactive component, configured to generate, upon the signal being supplied to the electric circuit, a magnetic field having both the first dominant frequency and the second dominant frequency, by virtue of the reactive component simultaneously resonating at both the first dominant frequency and the second dominant frequency,
wherein the reactive component is a first inductor, and wherein the electric circuit further comprises:
a first capacitor, connected in series with the first inductor;
a second inductor, connected in parallel with the first inductor; and
a second capacitor, connected in parallel with the first inductor and in series with the second inductor,
wherein the first capacitor and the first inductor are configured to resonate, collectively, at the first dominant frequency, and
wherein the second capacitor, the first inductor, and the second inductor are configured to resonate, collectively, at the second dominant frequency, and
wherein the first capacitor is configured to have an impedance having a magnitude of less than 20 Ohm at the second dominant frequency, and the second capacitor is configured to have an impedance having a magnitude of greater than 1000 Ohm at the first dominant frequency.

2. An apparatus, comprising:
a signal generator, configured to supply a signal having both a first dominant frequency and a second dominant frequency; and
an electric circuit, comprising a reactive component, configured to generate, upon the signal being supplied to the electric circuit, a magnetic field having both the first dominant frequency and the second dominant frequency, by virtue of the reactive component simultaneously resonating at both the first dominant frequency and the second dominant frequency,
wherein a difference between the first dominant frequency and the second dominant frequency is at least 5 kHz, and
wherein the first dominant frequency is less than 5 kHz, and the second dominant frequency is greater than 15 kHz.

3. An apparatus, comprising:
a signal generator, configured to supply a signal having both a first dominant frequency and a second dominant frequency; and
an electric circuit, comprising a reactive component, configured to generate, upon the signal being supplied to the electric circuit, a magnetic field having both the first dominant frequency and the second dominant frequency, by virtue of the reactive component simultaneously resonating at both the first dominant frequency and the second dominant frequency,
at least one first sensor, configured to generate a first signal in response to sensing the magnetic field at the first dominant frequency; and
at least one second sensor, configured to generate a second signal in response to sensing the magnetic field at the second dominant frequency, and
an intrabody tool comprising the first sensor.

4. A method, comprising the steps of:
using a signal generator, supplying, to an electric circuit that includes a reactive component, a signal having both a first dominant frequency and a second dominant frequency;
using the electric circuit, generating, upon the signal being supplied to the electric circuit, a magnetic field having both the first dominant frequency and the second dominant frequency, by virtue of the reactive component simultaneously resonating at both the first dominant frequency and the second dominant frequency;
using at least one first sensor, generating a first signal in response to sensing the magnetic field at the first dominant frequency;
using at least one second sensor, generating a second signal in response to sensing the magnetic field at the second dominant frequency; and in response to the first signal and the second signal, ascertaining respective locations of the first sensor and the second sensor.

5. The method according to claim 4, wherein using the first sensor to generate the first signal comprises using the first sensor to generate the first signal while the first sensor is inside a body of a subject.

6. The method according to claim 5, wherein generating the magnetic field comprises generating the magnetic field from beneath the subject.

7. A method, comprising the steps of:
using a signal generator, supplying, to an electric circuit that includes a reactive component, a signal having both a first dominant frequency and a second dominant frequency;
using the electric circuit, generating, upon the signal being supplied to the electric circuit, a magnetic field having both the first dominant frequency and the second dominant frequency, by virtue of the reactive component simultaneously resonating at both the first dominant frequency and the second dominant frequency;
wherein a difference between the first dominant frequency and the second dominant frequency is at least 5 kHz, and
wherein the first dominant frequency is less than 5 kHz, and the second dominant frequency is greater than 15 kHz.

\* \* \* \* \*